(12) United States Patent
King et al.

(10) Patent No.: US 8,001,970 B2
(45) Date of Patent: Aug. 23, 2011

(54) POSITIONING DEVICE FOR USE WITH A PATIENT UNDER ANESTHESIA AND ASSOCIATED METHODS

(75) Inventors: April Christine King, Cardiff by the Sea, CA (US); Adrian Pelkus, Escondido, CA (US); William J. Mazzei, San Diego, CA (US); Warren Gee Young, San Diego, CA (US)

(73) Assignee: Hypnoz Therapeutic Devices, Inc., San Diego, CA (US)

( * ) Notice: Subject to any disclaimer, the term of this patent is extended or adjusted under 35 U.S.C. 154(b) by 355 days.

(21) Appl. No.: 12/209,003

(22) Filed: Sep. 11, 2008

(65) Prior Publication Data

US 2010/0062391 A1    Mar. 11, 2010

(51) Int. Cl.
*A61G 15/00* (2006.01)
*A61H 1/00* (2006.01)
*A61F 5/00* (2006.01)
*A47C 17/02* (2006.01)

(52) U.S. Cl. ............... 128/845; 601/39; 602/18; 5/622

(58) Field of Classification Search ............ 128/845, 128/846, 848, 857, 869, 870; 601/41, 42, 601/43, 44, 39; 602/18, 32, 33; 297/391; 5/617, 622, 630, 636, 637, 638

See application file for complete search history.

(56) References Cited

U.S. PATENT DOCUMENTS

| 2,386,134 | A | | 10/1945 | Mermis |
| 3,596,655 | A | * | 8/1971 | Corcoran ................ 602/32 |
| 5,090,073 | A | | 2/1992 | Nordan et al. |
| 5,281,001 | A | * | 1/1994 | Bergsten et al. ......... 297/411.24 |
| 5,524,639 | A | | 6/1996 | Lanier et al. |
| 7,055,524 | B1 | * | 6/2006 | Taimoorazy ............ 128/845 |
| 7,096,869 | B1 | * | 8/2006 | Orlewicz et al. ........ 128/845 |
| 2005/0160532 | A1 | * | 7/2005 | Froelich ................. 5/637 |
| 2010/0000548 | A1 | | 1/2010 | Haworth et al. |

* cited by examiner

*Primary Examiner* — Patricia Bianco
*Assistant Examiner* — Ophelia Hawthorne
(74) *Attorney, Agent, or Firm* — Sheppard Mullin Richter & Hampton LLP

(57) ABSTRACT

The present invention provides devices for use with a patient under anesthesia and associated methods. Various embodiments of the present invention include a device for establishing and maintaining a patient's head and/or jaw in a particular position, including the sniffing position. Embodiments also include a method for positioning a patient comprising the use of a device of the present invention, wherein the device may substantially maintain a patient in a desired position.

21 Claims, 12 Drawing Sheets

POSITIONING DEVICE FOR USE WITH A PATIENT UNDER ANESTHESIA AND ASSOCIATED METHODS

FIELD OF THE INVENTION

The invention relates to surgical devices for positioning a patient, including a patient under general anesthesia or sedation, and in some embodiments to surgical devices for establishing and maintaining a patient's head and/or jaw in a particular position.

BACKGROUND OF THE INVENTION

Millions of surgeries and invasive diagnostic procedures are performed in the United States every year. Most, if not all, of these surgeries and procedures involve the use of some form of anesthesia or sedation. In some cases, general anesthesia is used that renders the patient unconscious. Generally, before and/or during such surgeries, a doctor (an "anesthesiologist" or an "oral surgeon") and/or Certified Registered Nurse Anesthetist) administers the anesthetics and monitors the patient while the patient is under anesthesia or sedation.

The job of the anesthesiologist or anesthetist is not a simple one. With modern anesthesia, a wide variety of medical equipment may be used. Anesthesia practitioners must possess a comprehensive and intricate knowledge of the use of various medical gases, anesthetic agents and vapors, medical breathing circuits and the variety of anesthetic machines (e.g., vaporizers, ventilators and pressure gauges) and their corresponding safety features, hazards and limitations. Moreover, a patient being treated under general anesthetics must be monitored continuously to ensure the patient's safety. For minor surgery, this generally includes monitoring of things such as heart rate, oxygen saturation, non-invasive blood pressure, inspired and expired gases (for oxygen, carbon dioxide, nitrous oxide, and volatile agents). For moderate to major surgery, monitoring may also include temperature, urine output, invasive blood pressure measurements, pulmonary artery pressure and pulmonary artery occlusion pressure, cerebral activity, neuromuscular function, and cardiac output. The various pieces of equipment and considerations can keep an anesthesiologist or anesthetist quite occupied before, during and after a surgical procedure.

Not surprisingly, an important consideration while a patient is under sedation or general anesthesia is insuring the patient can breathe properly. In some instances physically invasive methods, such as the insertion of tubes, are required. It has been shown, however, that positioning of the patient plays a role in ensuring the patient can breathe properly. For example, placing and keeping a patient in certain positions (e.g., the "sniffing" position) helps to ensure that a patient's airways is not obstructed. Thus, positioning of the patient is another condition that an anesthesiologist or anesthetist may need to monitor during a procedure. Therefore a method or device that aids the placing of a patient in a position that facilitates breathing and/or maintains the patient in that position during a procedure may ease the burden on an attending anesthesia practitioner before, during and after a surgical or similar procedure. Such a method or device may have broad applications in medicine and dentistry, including any situation where a patient is unconscious and/or immobilized whether or not that patient is under anesthesia.

SUMMARY OF THE INVENTION

In some embodiments, the present invention includes a device including: a base comprising a first side and a second side, wherein the base is configured to substantially accommodate a patient's head; a first support positioned on the first side of the base; a second support positioned on the second side of the base; a first mandible arm positioned on the first support, wherein the first mandible arm is configured to contact a patient's jaw; a second mandible arm positioned on the second support, wherein the second mandible arm is configured to contact a patient's jaw; wherein the first mandible arm and the second mandible arm are movable in three axes such that each is positionable to be in contact with a patient's jaw and to maintain a patient in a desired position. In certain embodiments, the base is rectangular. In some embodiments, the mandible arm is positionable to be in contact with a patient's jaw at three points. In further embodiments, the first mandible arm and the second mandible arm each include a mandible pad. In yet further embodiments, the first mandible arm and the second mandible arm are removably connected to the first support and the second support, respectively. In other embodiments, the first mandible arm is movable relative to the first support and the second mandible arm is movable relative to the second support. In some embodiments, the three axes are the x, y and w axes relative to the patient. In various embodiments, the desired position is the sniffing position. In certain embodiments, the mandible pad comprises foam. In further embodiments, the mandible arm is positionable such that the mandible pad is in contact with a patient's jaw at one or more points. In some embodiments, the mandible arm is positionable such that the mandible pad is in contact with a patient's jaw at three points. In yet other embodiments, the first support is movable relative to the base and the second support is movable relative to the base. In various embodiments, the first support is movable relative to the base in two axes and the second support is movable relative to the base in two axes. In some embodiments, the first support is movable relative to the base in three axes and the second support is movable relative to the base in three axes. In other embodiments, the first support is movable relative to the first mandible arm and the second support is movable relative to the second mandible arm.

In other embodiments the present invention includes a device including: a base comprising a plurality of supports, wherein the base is configured to substantially accommodate a patient's head, wherein each support comprises a mandible arm, wherein each mandible arm is configured to contact a patient's jaw; and wherein each mandible arm is movable in three axes such that each mandible arm is positionable to be in contact with a patient's jaw and to maintain a patient in a desired position. In certain embodiments, the base is rectangular. In other embodiments, each mandible arm is positionable to be in contact with a patient's jaw at three points. In further embodiments, each mandible arm comprises a mandible pad. In yet further embodiments, each mandible arm is removably connected to each support. In some embodiments, each mandible arm is movable relative to a support. In other embodiments, the three axes are the x, y and w axes relative to the patient. In yet other embodiments, the desired position is the sniffing position. In various embodiments, each mandible pad includes foam. In certain embodiments, each mandible arm is positionable such that the mandible pad is in contact with a patient's jaw at one or more points. In certain embodiments, each mandible arm is positionable such that the mandible pad is in contact with a patient's jaw at three points. In further embodiments, each support is movable relative to the base. In yet further embodiments, each support is movable relative to the base in two axes. In other embodiments, each support is movable relative to the mandible arms.

In other embodiments, the present invention includes methods. The method may be a method for positioning a patient including the steps of: providing any embodiment of the devices of the present invention, placing the patient's head substantially on the base of the device; placing the patient's head in a desired position; moving a first mandible arm to contact the patient's jaw; moving a second mandible arm to contact the patient's jaw; wherein the contact of the first mandible arm and the second mandible arm provides sufficient force to substantially maintain the patient's head and/or jaw in a desired position.

In yet other embodiments, the present invention includes a mandible arm including: a curved portion, wherein the curved portion is substantially rigid; a mandible pad, wherein the mandible pad is flexible, and wherein the mandible pad has a distal side configured to attach to the curved portion and a proximal side configured to contact a patient's jaw at a plurality of points; and a connector portion wherein the connector portion is configured to attach to a support. In some embodiments, the mandible arm may be adapted to work with any embodiment of the devices of the present invention. In other embodiments, the mandible pad comprises foam. In yet other embodiments, the connector portion is configured to attach to a support that is attached to a base comprising a left side and a right side, wherein the base is configured to substantially accommodate a patient's head, and wherein the support is movable in three axes such that the mandible pad is positionable to be in contact with a patient's jaw at one or more points and to maintain a patient in a desired position.

DETAILED DESCRIPTION

Figure 1:
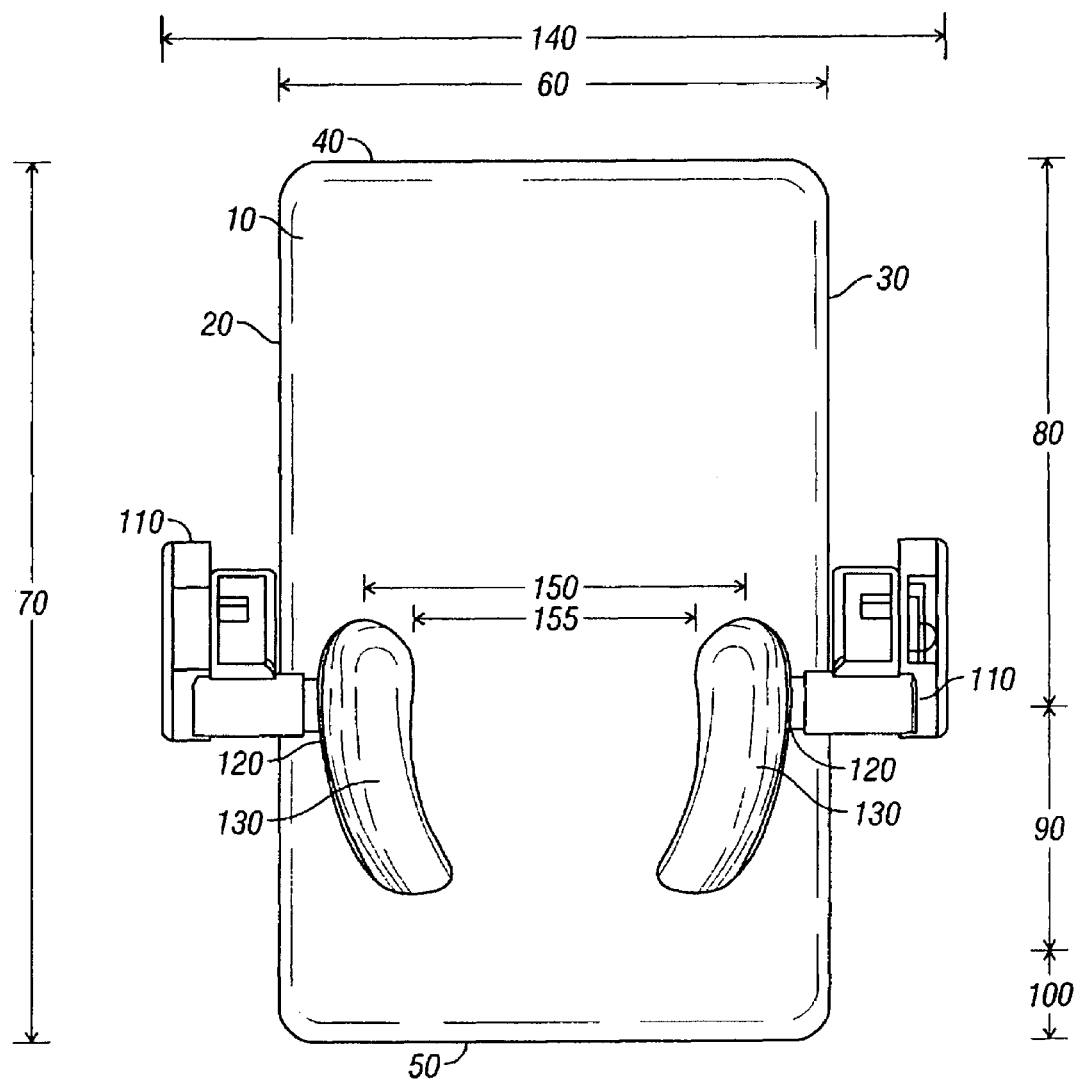
FIG. 1 is a schematic diagram providing a top view of an embodiment of a device of the present invention.

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

It is understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a support" is a reference to one or more supports and includes equivalents thereof known to those skilled in the art and so forth.

The present invention includes devices and methods. The devices of the present invention include devices for positioning a patient. In some embodiments, the devices may be used for positioning and/or maintaining a patient in a given position before, during and/or after a medical (including surgical), dental or diagnostic procedure. In many embodiments, the patient is under sedation or general anesthesia, and in some embodiments the patient may be rendered unconscious by general anesthesia. In some embodiments, the positioning of the patient facilitates or eases the breathing of the patient, for example by ensuring anatomical alignment of the patient's airway. The devices may position the patient in the "sniffing" position or a similar position. The devices of the present invention may, for example, allow an anesthesiologist or anesthetist place and maintain a patient in a desired position. In some embodiments the devices of the present invention permit a person to place a patient in a specific position in a quick and efficient manner. The devices of the present invention have applications in both medicine and dentistry and references to a "procedure" or a "surgical procedure" refer to various medical procedures, diagnostic procedures and dental procedures, including oral surgeries, root canals, removal of teeth, and others.

The methods of the present invention include methods of positioning a patient. Some methods may include the positioning and/or maintaining of a patient in a given position before, during and/or after a surgical, diagnostic or dental procedure. Some methods of the present invention may involve the use of a device of the present invention. Some embodiments involve the positioning of a patient in a position that may ease or facilitate the breathing of the patient, for example the "sniffing" position. In many embodiments, the patient is under sedation or anesthesia, including a patient that is rendered unconscious by general anesthesia or sleepy after general anesthesia.

With reference to FIG. 1, an embodiment of a device of the present invention is illustrated. Base 10 is depicted as having left side 20, right side 30, upper side 40, and lower side 50. In the illustrated embodiment, base 10 is rectangular, but it may have any suitable shape. Base 10 may be made of any suitable material, including materials that are Magnetic Resonance Imaging ("MRI") compatible, washable and/or sterilizable. In some embodiments, base 10 may be made of medical grade plastic or closed-cell foam. Base 10 may also be made of various other MRI compatible materials, including plastics, resins, resinoids, polymers, cellulose derivatives, casein materials, and metals. Base 10 may also include a cover on all or a portion of base 10. For example, such cover may be made of soft or hard foam, fabric, or cushioned material. Such materials may also be integral with a portion of base 10.

In some embodiments, base 10 may also have an alignment guide 155. Although alignment guide 155 is illustrated as an alignment line in FIG. 1, it may be any suitable structure or element. For example, alignment guide 155 may be an outline, an arrow, a notch or series of notches, an indentation, or any suitable structure. Alignment guide 155 provides a visual guide to a person attempting to place a patient in a desired position. Thus, alignment guide 155 may be movable or have multiple positions or designations that depend upon the desired position of the patient. In embodiments where alignment guide 155 is a line on base 10, the line may be approximately in line with the mandible arm 120; the patient's lip may then be placed approximately in line with the alignment guide 155. In addition, the patient is adjusted such that the mandible pad 130 may align with the patient's jaw.

Figure 2A:
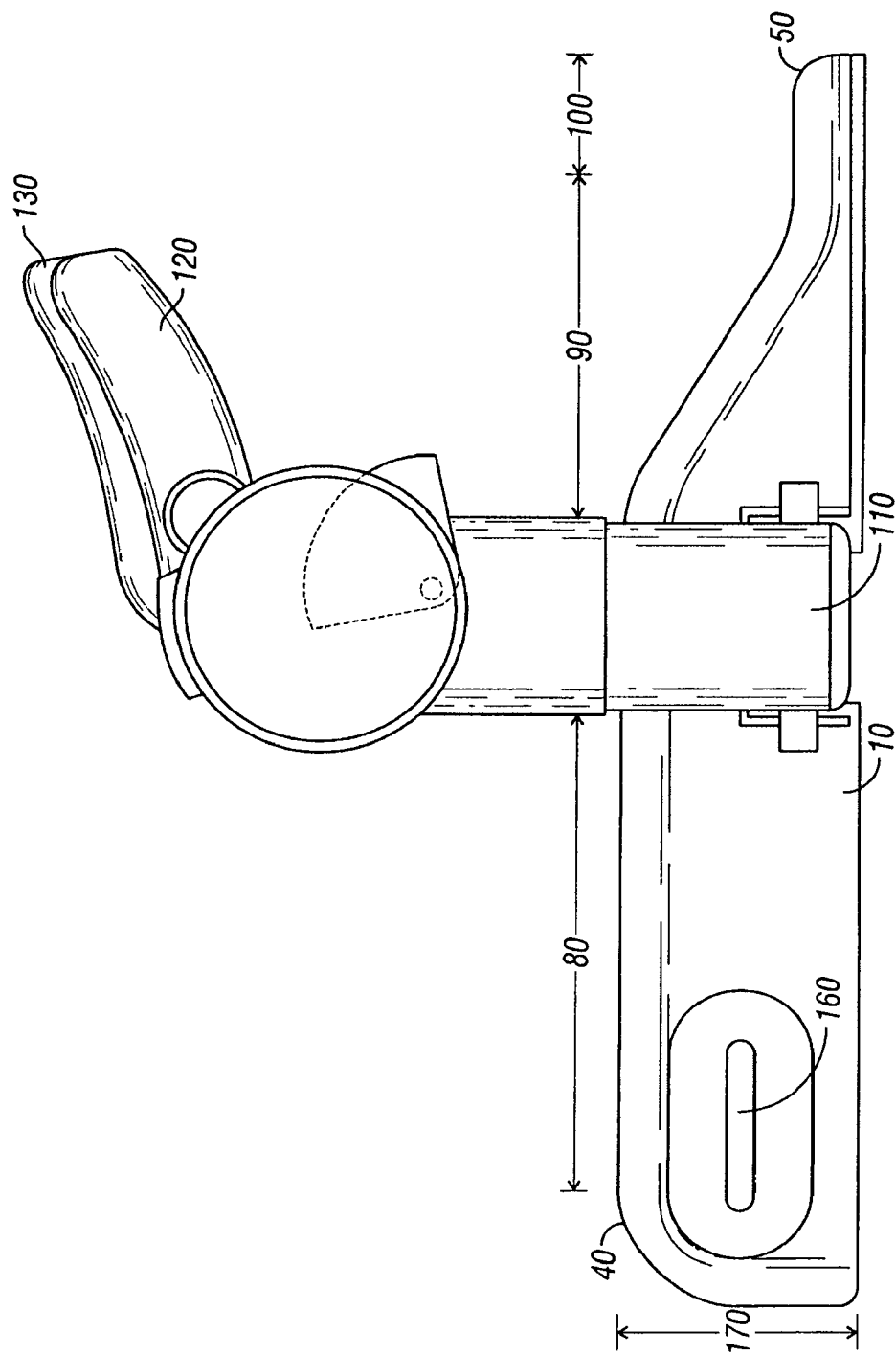
FIGS. 2A-2B are schematic diagrams providing a side view of an embodiment of the present invention.
Figure 2B:
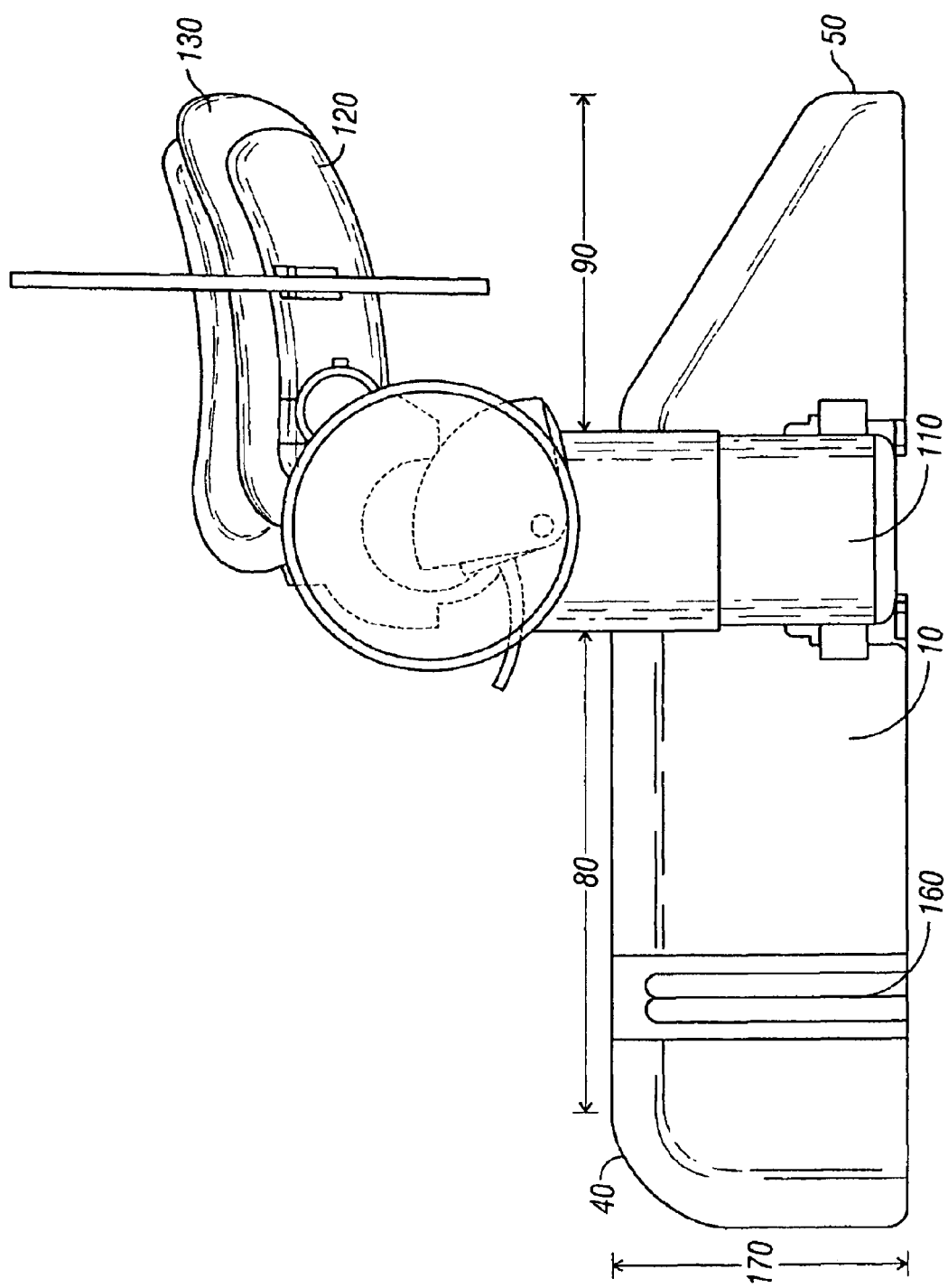

With reference to FIGS. 2A-B, gripping element 160 is also depicted. Gripping element 160 may be any suitable structure having any suitable size and configuration. For example, gripping element 160 may be a protrusion or a depression, or any other structure or texture that facilitates movement of base 10 by a person.

Returning to FIG. 1, base 10 has width 60 and length 70. Width 60 may be any suitable width and may be substantially uniform or substantially non-uniform along length 70. Generally, width 60 is sufficient to accommodate, or substantially accommodate, the width of the head of a patient. In some embodiments, width 60 may vary depending upon the intended or desired use of a particular device—for example a base 10 that is to be used for pediatric patients may have a width 60 that is less than the width 60 of a base 10 that is to be used for adult patients. In other embodiments base 10 has a width 60 that is usable with both adult and pediatric patients. In certain embodiments, width 60 may be from about three inches to about eighteen inches. In other embodiments, width 60 may be from about six to about ten inches. In further embodiments, width 60 may be about six and three quarters inches.

Similarly, length 70 may be any suitable length. Generally, length 70 is sufficient to accommodate, or substantially accommodate, the length of the head of a patient. Length 70 may also be sufficient to accommodate, or substantially accommodate, a patient's neck. In some embodiments, length 70 may vary depending upon the intended or desired use of a particular device—for example a base 10 that is to be used for pediatric patients may have a length 70 that is less than the length 70 of a base 10 that is to be used for adult patients. In other embodiments base 10 has a length 70 that is usable with both adult and pediatric patients. In certain embodiments, length 70 may be from about eight inches to about thirty-six inches. In other embodiments, length 70 may be from about twelve to about twenty-four inches. In some embodiments, length 70 may be divided into one or more zones or areas having different characteristics, including one or more of material, height, and grade (or slope). Length 70 may have any suitable number of zones having any suitable characteristics. In the illustrated embodiment, length 70 is separated into three zones: raised zone 80, sloped zone 90, and depressed zone 100.

FIG. 2A depicts a side view of left side 20 of an embodiment of the present invention. The side view better illustrates an embodiment having raised zone 80, sloped zone 90, and depressed zone 100, such that the differences in the depicted zones are more readily apparent. Raised zone 80 is generally disposed near upper side 40 and has a height 170 that is greater than the height of depressed zone 100, which is generally disposed near lower side 50. Sloped zone 90 comprises the transition from the greater height 170 of raised zone 80 to the lower height of depressed zone 100. Sloped zone 90 may have a constant or variable slope and the slope may be of any suitable magnitude. In some embodiments, raised zone 80, sloped zone 90 and depressed zone 100 are generally configured to accommodate a patient's head and neck, with sloped zone 90 approximately in line with the patient's neck. FIG. 2B shows an embodiment similar to FIG. 2A. FIG. 2B depicts an embodiment of base 10 having only a raised zone 80 and sloped zone 90.

Height 170 may be any suitable height. Preferably, height 170 is sufficient to raise a patient's head a suitable distance such that the patient's head may be placed in the "sniffing" position or such other position as may be desired, for example to provide improved, eased or consistent breathing by the patient. As discussed above, height 170 may be constant over length 70 or it may be variable. In some embodiments, height 170 may be from about one quarter of an inch to about six inches. In other embodiments, height 170 may be from about one inch to about three inches. In some embodiments the height of raised zone 80 is from about two inches to about four inches and the height of depressed zone 100 is from about one quarter of an inch to about one inch.

Returning to FIG. 1, base 10 is depicted with a support 110 on each of right side 30 and left side 40. Support 110 may be integral with base 10 or support 110 may be removable from base 10. Each support 110 is attached to a mandible arm 120 having a mandible pad 130. In some embodiments both the support width 140 and the mandible gap 150 are adjustable. Support width 140 represents the distance from the outside edge of one support 110 to the outside edge of the opposite support 110. In some embodiments, support width 140 is adjustable by movement of support 110 (or by varying the width of base 10). Support width 140 may be any suitable width, but generally is a width sufficient to accommodate the width of the head of a patient. In some embodiments, support width 140 may be from about two to about twelve inches, from about four to about eight inches, from about five to about seven inches, about eight inches, or any suitable width or range of widths. Mandible gap 150 represents the distance between the medial edge of mandible arm 120 on one side of base 10 to the medial edge of mandible arm 120 on the opposite side of base 10. In some embodiments, mandible gap 150 is adjustable by movement of support 110 and/or mandible arm 120. Mandible gap 150 may be any suitable distance, but generally is a distance sufficient to accommodate the width of a patient's jaw. In some embodiments, mandible gap 150 may be from about two to about eight inches, from about three to about six inches, from about three to about five inches, about five inches, or any suitable distance or range of distances.

Figure 3A:
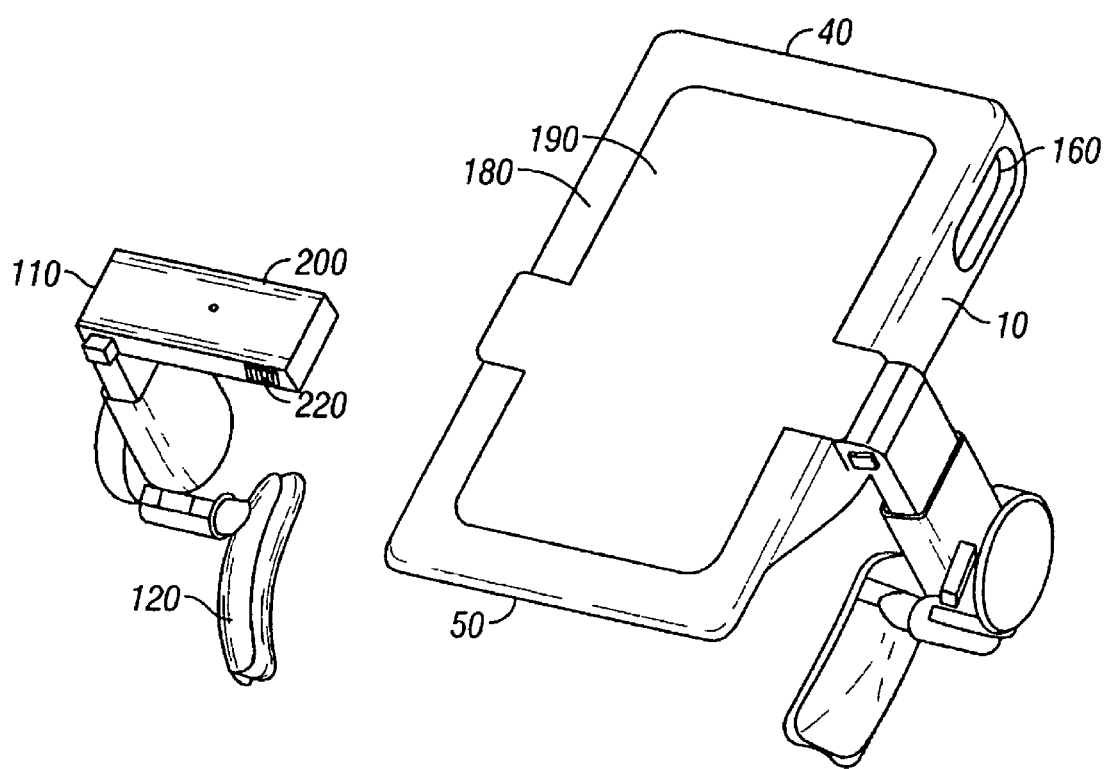
FIGS. 3A-3B are schematic diagrams of an embodiment of a device of the present invention.

FIG. 3A illustrates a bottom view of an embodiment of a device of the present invention. Bottom surface 180 of base 10 is depicted. In this embodiment bottom surface 180 has non-skid surface 190. Other embodiments of bottom surface 180 may not have non-skid surface 190 and may have other suitable structures or features. Non-skid surface 190 may be any surface that permits movement of base 10 when the patient is not on base 10, yet inhibits movement of base 10 when a patient is placed on base 10. Non-skid surface 190 may encompass all or only a part of bottom surface 180. For example, non-skid surface 190 may be a rubberized or tacky surface, a textured surface, or any other suitable substance or texture.

Figure 3B:
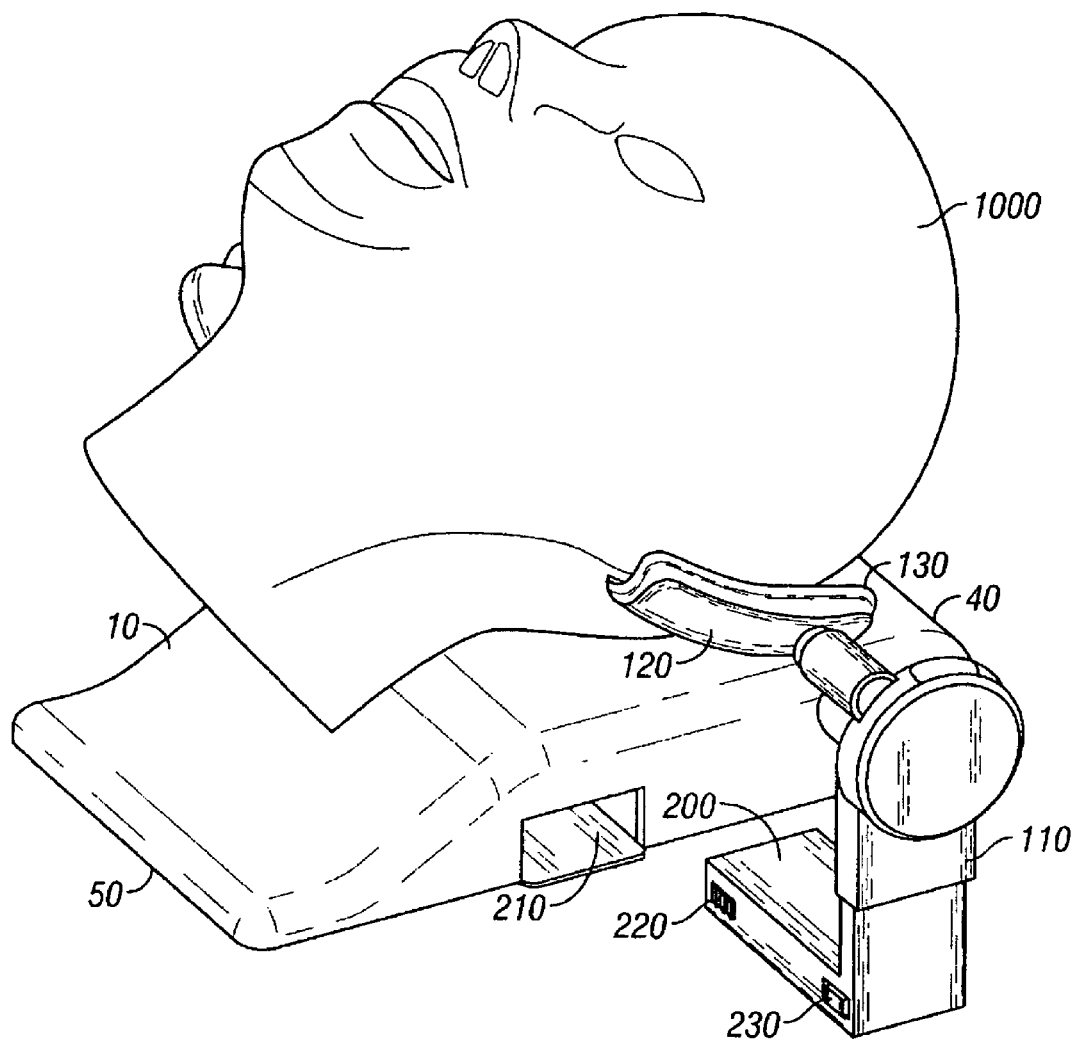

FIG. 3A depicts an embodiment having a support 110 that may be removably attached to base 10. In other embodiments, support 110 may be fixedly attached to base 10 or integral with base 10. Support 110 is illustrated having an insertion portion 200. With reference to FIG. 3B, a patient 1000 is depicted on base 10. Also illustrated is a slot 210. Insertion portion 200 is configured to fit within slot 210. In turn, slot 210 is configured to receive insertion portion 200. Although slot 210 and insertion portion 200 are depicted as rectangular, each may have any suitable shape, size or configuration. For example, slot 210 and insertion portion 200 may be cylindrical, triangular, or any other suitable shape. In addition, slot 210 and insertion portion 200 could also be a plurality of slots and/or insertion portions. For example, insertion portion 200 could comprise two rectangular portions configured to insert into a slot 210 that comprises two rectangular slots.

Continuing with reference to FIG. 3A, in some embodiments insertion portion 200 has a connector 220 that is engageable with an element within slot 210 such that insertion portion 200 is locked into a position or is lockable into a variety of positions once inserted into slot 210. Connector 220 may be any suitable structure having any suitable configuration. In some embodiments, connector 220 may be a grooved structure that protrudes from insertion portion 200 such that it extends to engage an element within slot 210. In some embodiments, button 230 may be used to selectively engage/disengage (e.g., extend and/or retract) connector 220, such that insertion portion 200 may be pushed into or pulled out of slot 210 in selected increments. With reference back to FIG. 1, such movement may adjust support width 140 and/or mandible gap 150. Button 230 may be any suitable structure may be used to control the degree of insertion of insertion portion 210. Support 110 is described in greater detail with reference to FIGS. 5A-5B.

FIGS. 4A-4E provide close-ups of embodiments of mandible arm 120. Mandible arm 120 may be custom sized to fit a particular patient or it may be sized such that it fits a number of patients. For example, mandible arm 120 may be smaller for pediatric patients than for adult patients, or mandible arm 120 may be available in a variety of sizes. Mandible arm 120 may be removably or fixedly attached to support 110 or it may be integral with support 110. In some embodiments, mandible arm 120 may be disposable, but in other embodiments it may be reusable, washable, and/or sterilzable. In some embodiments the shape of mandible arm 120 is such that a patient may be engaged with a device of the present invention and have a standard oxygen mask attached over the patient's mouth and/or nose.

In the depicted embodiment, mandible arm 120 includes mandible pad 130, curved portion 300 and arm portion 340. Curved portion 300 may be made of any suitable material and may have any suitable configuration. In preferred embodiments, curved portion 300 is substantially rigid, elongate, concave and has a curvature that facilitates effective contact with a patient's jaw. In some embodiments, the shape of curved portion 300 provides shape to mandible pad 130. In some embodiments, curved portion 300 is configured such that mandible arm 120 is configured to contact a patient's jaw at one or more points. In some embodiments, curved portion 300 is configured to contact the patients jaw at two or three points. In certain embodiments, curved portion 300 is configured to facilitate contact of mandible arm 120 with the ramus of a patient's jaw, the body of the patient's jaw and the angle of a patient's jaw. In other embodiments, curved portion 300 may be non-rigid, or have non-rigid portions, and may even be substantially lacking in curvature. In certain embodiments, curved portion 300 is made of a medical grade plastic, but curved portion 300 may be made of other materials, such as various other plastics, resins, resinoids, polymers, cellulose derivatives, casein materials, glass, and metals.

Figure 4A:
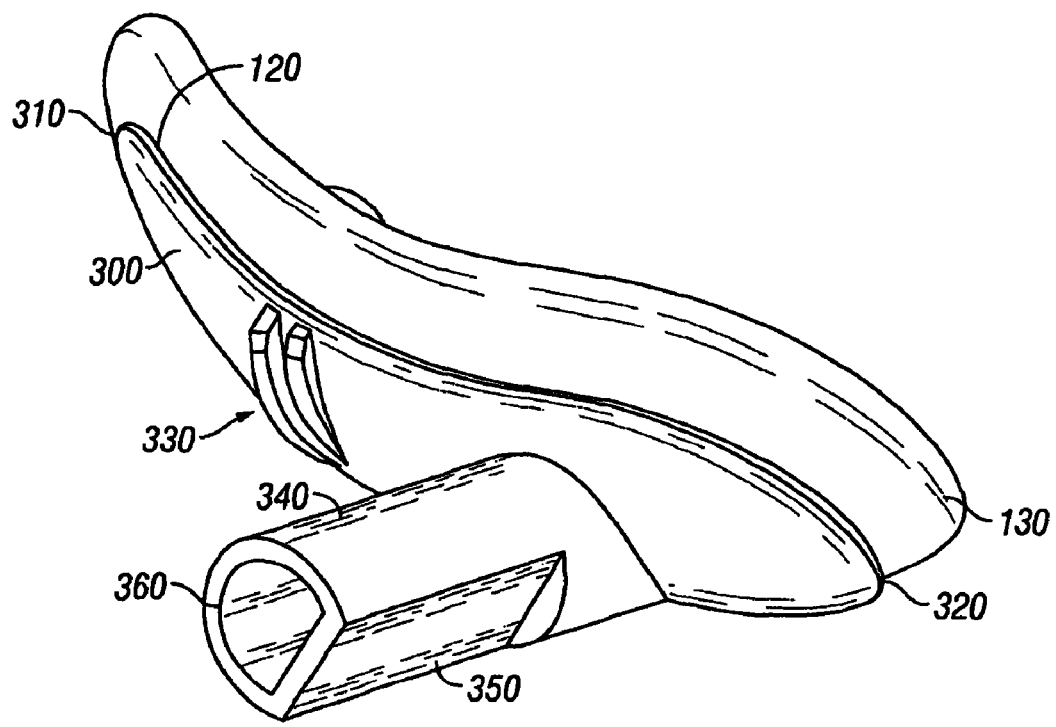
FIGS. 4A-4E are schematic diagrams providing multiple views of embodiments of a mandible pad of the present invention.
Figure 4B:
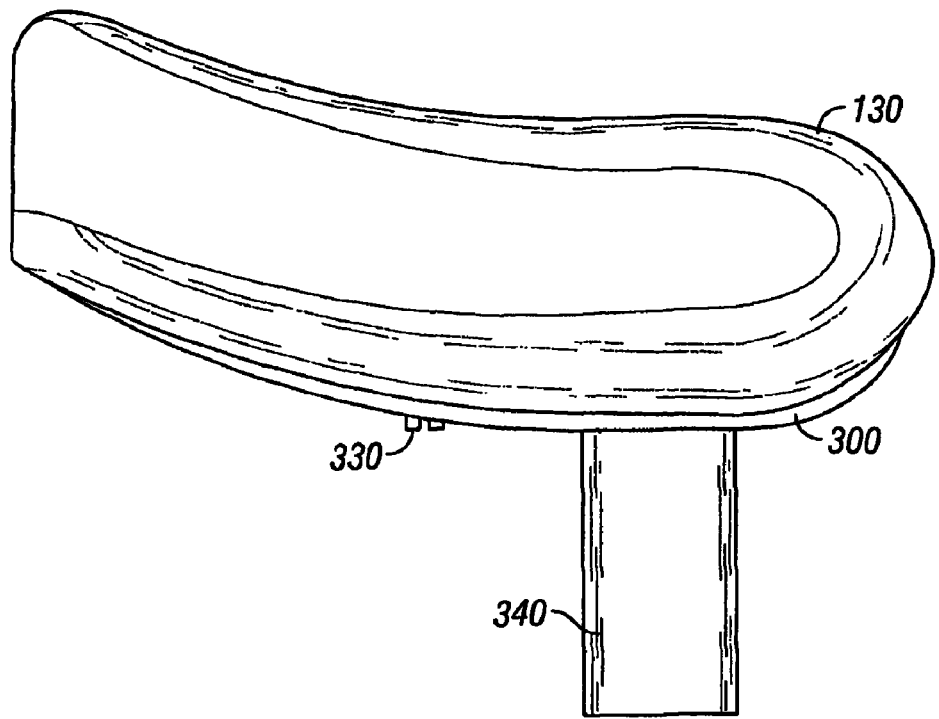

Curved portion 300 is illustrated as having lower end 310 and upper end 320. In the illustrated embodiments, lower end 310 is oriented toward lower side 50 of base 10 and upper end 320 is oriented toward upper side 40 of base 10. Also depicted on curved portion 300 is tubing grip 330. Tubing grip 330 may be any structure or structures configured to grip and hold tubing that may be attached to tools or equipment used during, prior to, or after a surgical, or similar, procedure is performed. For example, tubing grip 330 may be used to grip tubing that leads to an oxygen mask placed over the mouth and nose of a patient. In FIG. 4A, tubing grip 330 is illustrated as a pair of ribs spaced apart a suitable distance to permit the ribs to grip tubing without substantially impairing the flow of gas through the tubing. In FIG. 4D, tubing grip 330 is depicted as a pair of pillars also spaced apart a suitable distance to permit the ribs to grip tubing without substantially impairing the flow of gas through the tubing. In some embodiments the distance between the ribs and/or pillars is from about 1 mm to about 5 mm. In other embodiments, the distance between the ribs and/or pillars is about 2 mm. In yet further embodiments, the distance between the ribs and/or pillars is about 2.8 mm.

Returning to FIG. 4A, arm portion 340 extends medially from curved portion 300 and is configured to engage support 110. Although depicted as approximately cylindrical with flat surface 350, arm portion 340 may have any suitable shape, size and configuration, and may be made of any suitable material. Arm portion 340 may be removably or fixedly attached to support 110 and in some embodiments arm portion 340 may be integral with support 110. Arm portion 340 also may be keyed such that it will only attach to the appropriate support 110—for example, an arm portion 340 for use with a support 110 on left side 20 of base 10 may be configured such that it will only attach to that support 110. In the illustrated embodiment, arm portion 340 has flat surface 350 and medial end 360.

Figure 4C:
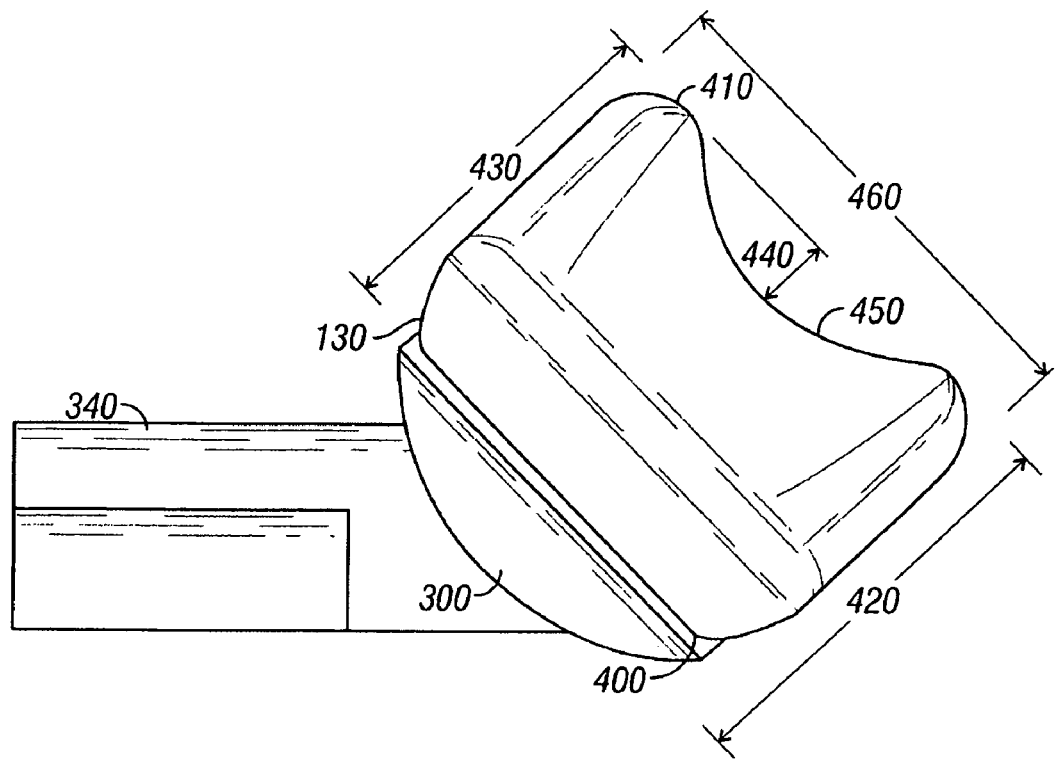
Figure 4D:
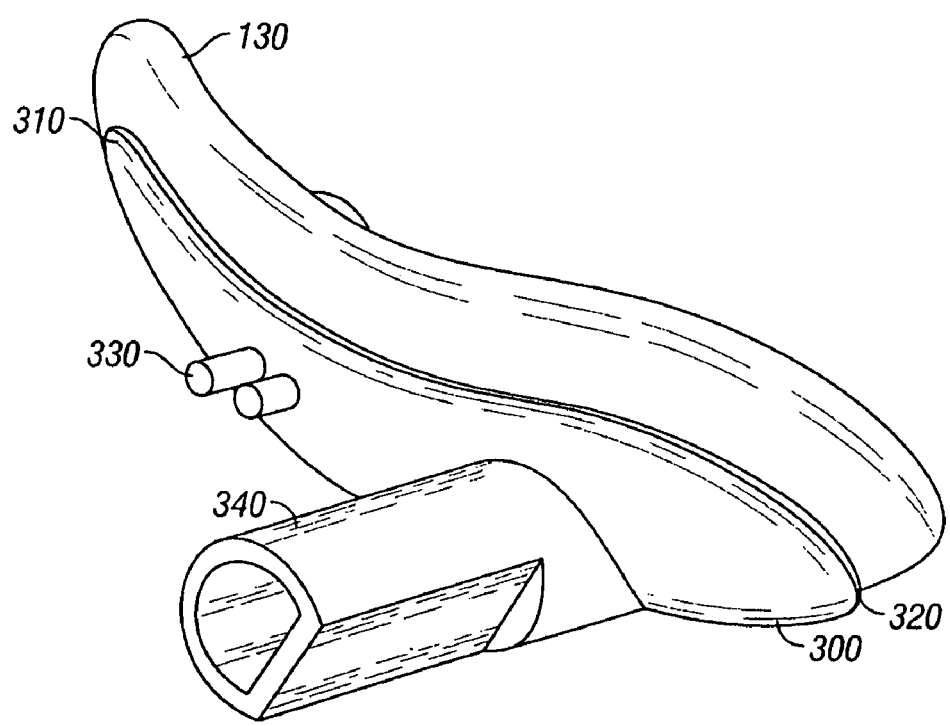

With reference to FIG. 4C, mandible pad 130 is highlighted. FIG. 4C illustrates mandible arm 120, with arm portion 340, curved portion 300 and mandible pad 130. Mandible pad 130 may be made of any suitable material having any suitable size, shape, and properties. In some embodiments, mandible pad 130 is elongate, but in other embodiments it may be oval, circular, rectangular or any other suitable shape. In certain embodiments mandible pad 130 may be flexible, but in other embodiments it may be malleable, resilient, rigid or any other suitable consistency. Mandible pad 130 may be made of molded or flat foam, but in other embodiments it may be made of medical grade plastic or moldover foam, other plastics, rubber, resins, metals or any other suitable material. In further embodiments mandible pad 130 may be disposable, but in other embodiments it may be reusable, washable, and/or sterilzable. Mandible pad 130 may be removably or fixedly attached to curved portion 300. In some embodiments mandible pad 130 may be attached by glue, epoxy, cement or the like, but in other embodiments mandible pad 130 may be attached to curved portion 300 in any suitable manner. In preferred embodiments, mandible pad 130 is made of flexible foam, elongate and fixably attached to curved portion 300 with a glue or epoxy.

In some embodiments, mandible pad 130 is configured to contact a patient's jaw at one or more points. In some embodiments, mandible pad 130 is configured to contact the patient's jaw at two or three points. For example, with reference to FIG. 6, a patient 1000 having jaw line 900 is depicted on a device of the present invention having base 10 with upper side 40, lower side 50, support 110, and mandible arm 120 having mandible pad 130. Jaw line 900 has multiple portions corresponding to different portions of the patient's jaw bone. Ramus 930 corresponds to the edge of the ramus of the patient's jaw bone, body 910 corresponds to the edge of the body of the patient's jaw bone, and angle 920 corresponds to the edge of the angle of the patient's jaw bone. In certain embodiments, mandible pad 130 is configured to contact the ramus 930 of a patient's jaw, the body 910 of the patient's jaw and the angle 920 of a patient's jaw. Of course, references to such contact here and in other portions of this disclosure do not refer to direct contact, but rather refer to indirect contact by contact of the patient's skin.

With reference now to FIG. 4C, mandible pad 130 has distal surface 400, medial surface 410, height 420, width 460 and extends distance 430 away from curved portion 300. Height 420 may be any suitable height. For example, height 420 may be from about one tenth of an inch to about 5 inches, from about one quarter of an inch to about one and a half inches, from about one half of an inch to one inch, or any other suitable height. Similarly, distance 430 may be any suitable distance. For example, distance 430 may be from about one tenth of an inch to about five inches, from about one quarter of an inch to about one and one half inches, from about one half of an inch to one inch, or any other suitable height. Additionally, width 460 may be any suitable width. For example, width 460 may be from about one eighth of an inch to about four inches, about one half of an inch to about two and a half inches, about one inch to about two inches, or any other suitable width. The depicted embodiment has a medial surface 410 that has depression 450 having depth 440. In other embodiments, medial surface 410 may be flat, substantially flat or even convex. Although depicted as rounded, depression 450 may have any suitable shape. In addition, medial surface 410 may have multiple depressions 450 of similar, different or identical configurations. Depression 450 may be uniform or substantially uniform along the length 470 (depicted in FIG. 4E) of mandible pad 130 or its presence or characteristics may vary over the length 470 of mandible pad 130. For example depth 440 of depression 450 may be substantially constant or may vary along the length 470 of mandible pad 130. Depth 440 may be any suitable depth from the highest point of medial surface 410. For example, depth 440 may be from about one sixteenth of an inch to about one inch, from about one eighth of an inch to about three quarters of an inch, from about one quarter of an inch to about one half of an inch, or any suitable depth. Similarly, length 470 may be any suitable length. For example, length 470 may be from about one inch to about seven inches, from about two inches to about five inches, from about two and one half inches to about four inches, about three and one half inches, or any other suitable length.

Figure 4E:
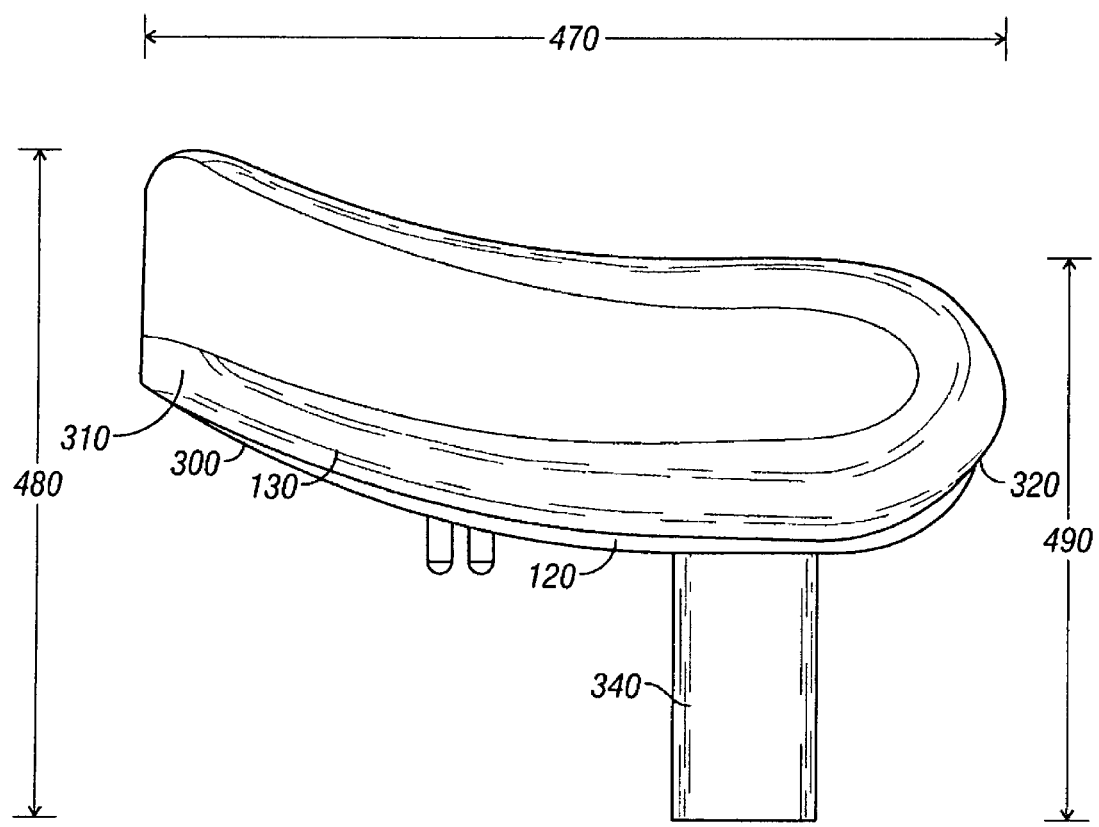

With reference to FIG. 4E is a top view of an embodiment of mandible arm 120 and mandible pad 130. This figure depicts length 470 as described above. This figure also illustrates an embodiment of mandible arm 120 that, because of the curvature of curved portion 300, has a first length 480 and a second length 490. In preferred embodiments first length 480 is greater than second length 490. In some embodiments, first length 480 is from about one inch to about five inches, from about one and a half inches to about four inches, from about two and a half inches to about three and a half inches, about three inches, or any other suitable length. In some embodiments, second length 490 is from about one half inch to about five inches, from about from about one inch to about four inches, from about two and inches to about three inches, about two and a half inches, or any other suitable length. In one embodiment, first length 480 is about three inches and second length 490 is about two and one half inches.

Figure 5A:
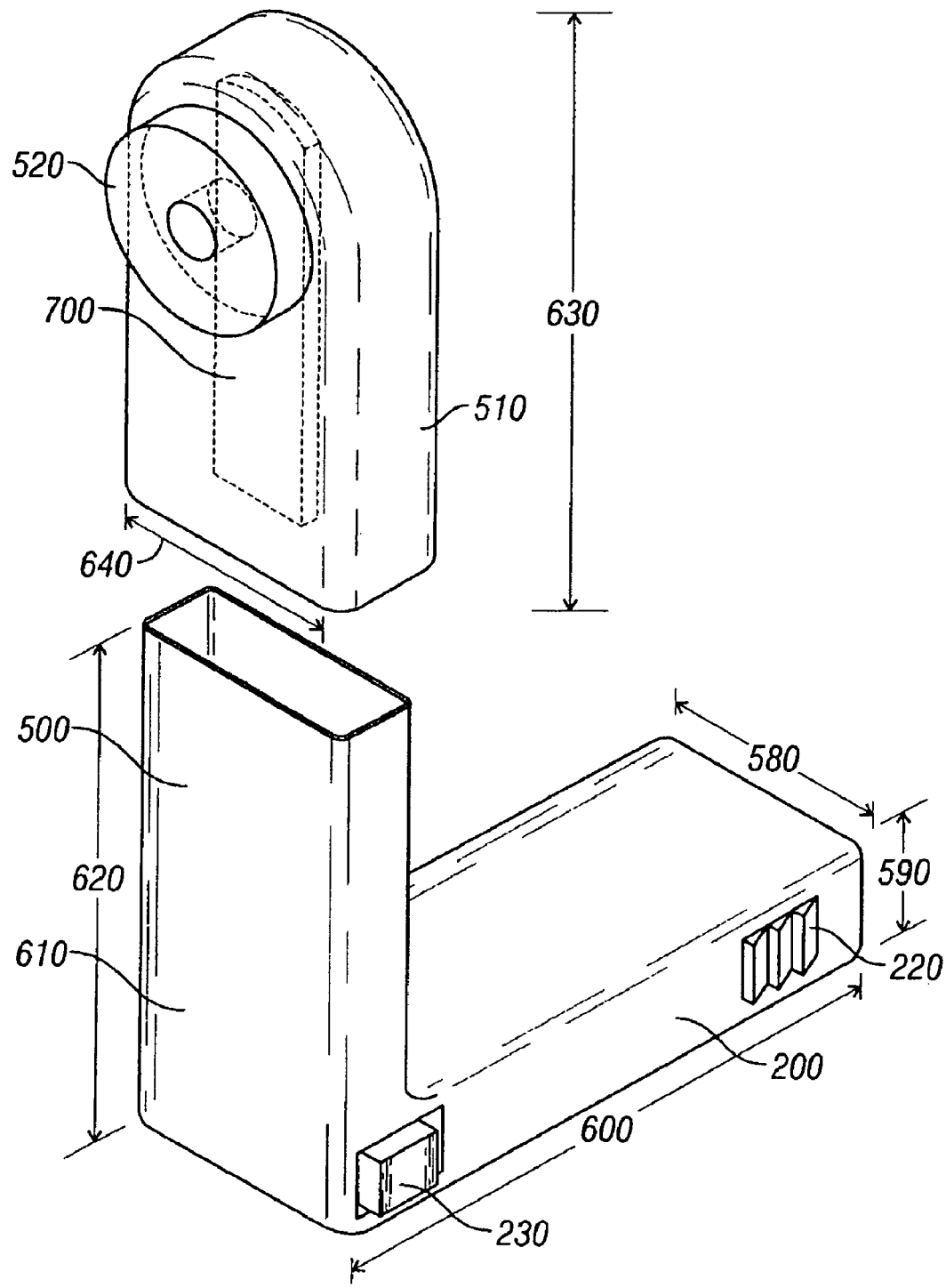
FIGS. 5A-5C are schematic diagrams of an embodiment of a support of the present invention.
Figure 5B:
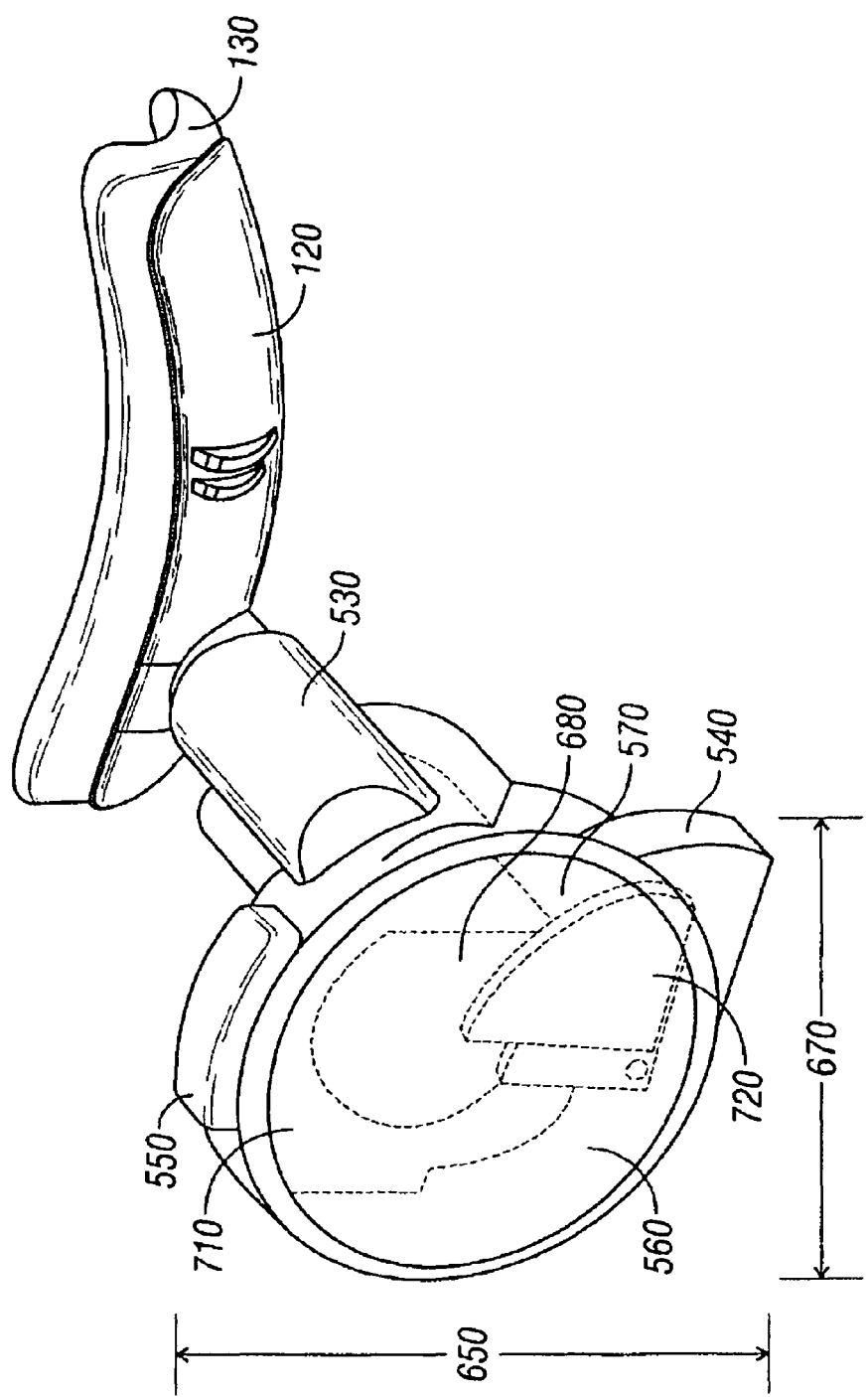
Figure 5C:
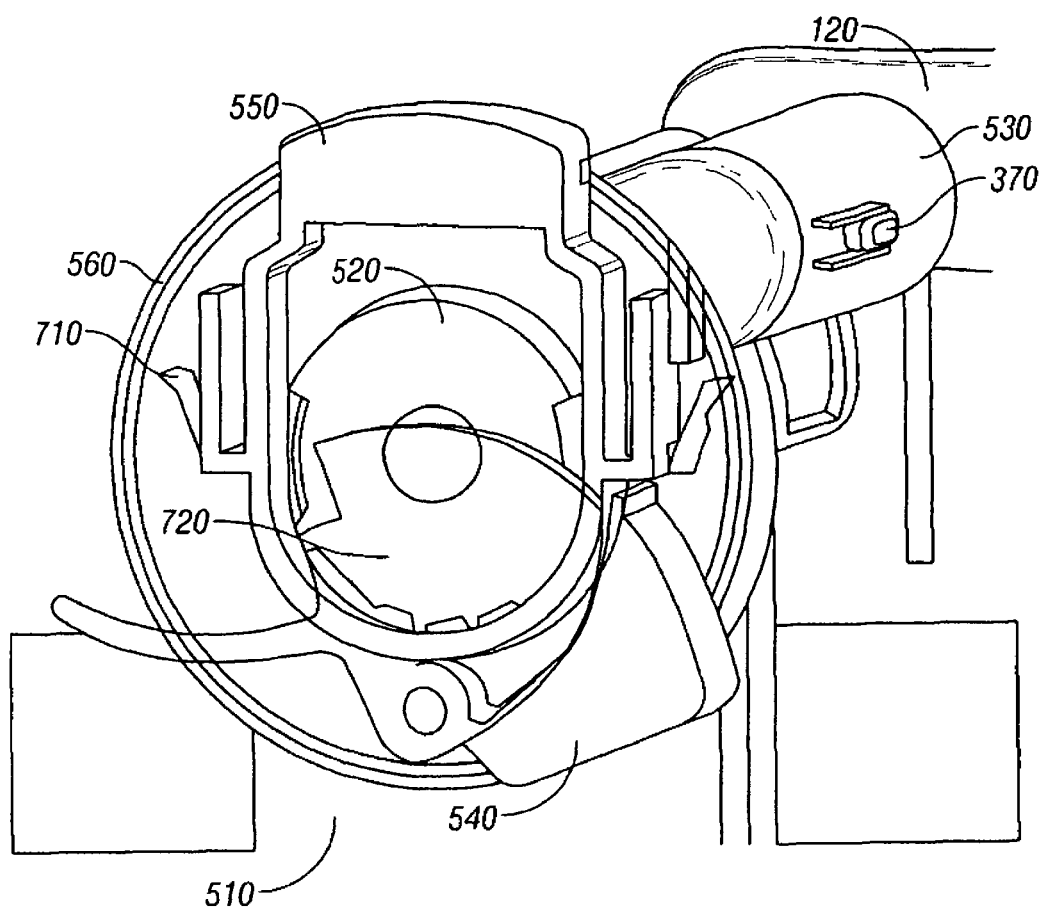

FIGS. 5A-5C are close-ups of embodiments of support 110. In the illustrated embodiment, support 110 has a first portion 500, a second portion 510 and a third portion 560 that may be removably or fixedly attached to each other and/or base 10. In other embodiments support 110 may be a unitary structure and/or may be integral with base 10 and/or mandible arm 120. Although depicted as having various parts having specific shapes and connections, support 110 may have any suitable configuration and have any suitable shape.

In preferred embodiments, support 110 is adjustable in at least one axis. In some embodiments support 110 is adjustable in an x-axis (for example, as defined by insertion portion 200 and mandible gap 150 (see FIG. 1) and/or a y-axis (for example, as defined by height 620 of upper portion 610). In other embodiments support 110 may also be adjustable in a z-axis (for example and with reference to FIG. 1, as defined by the edge of left side 20 of base 10) and/or a w-axis (for example, defined as by rotation of third portion 560). In preferred embodiments, support 110 is adjustable in at least the x, y and w axes.

In some embodiments, the adjustment of support 110 places mandible arm 120 in contact with a patient's jaw at two or three points. In some embodiments, adjustment of support 110 results in placing and/or holding the patient in a desired position. In some embodiments, the desired position is the sniffing position. For example, with reference to FIG. 6, a patient 1000 having jaw line 900 is depicted on a device of the present invention having base 10 with upper side 40, lower side 50, support 110, and mandible arm 120 having mandible pad 130. Jaw line 900 has multiple portions corresponding to different portions of the patient's jaw bone. In certain embodiments, support 110 is adjustable such that mandible arm 120 may be moved to contact the ramus 930 of a patient's jaw, the body 910 of the patient's jaw and the angle 920 of a patient's jaw.

With reference to FIG. 5A, an embodiment of first portion 500 of support 110 is depicted. First portion 500 has length 600, a first height 590, a second height 620, connector 220, button 230, insertion portion 200 and upper portion 610. Connector 220, button 230 and insertion portion 200 were described with reference to FIGS. 3A-3B. As illustrated, insertion portion 200 has length 600, width 580 and height 590, each of which may be any suitable magnitude. For example, length 600 may be from about one inch to about eight inches, from about two inches to about five inches, from about two and a half inches to about four inches, from about three to about three and a half inches, or any suitable length. For example, width 580 may be from about one half of one inch to about six inches, from about one inch to about three inches, from about one and a half inches and about two and a half inches, or any suitable width. For example, height 590 may be from about one eighth of an inch to about three inches, from about one quarter of an inch to about one and a half inches, from about a half an inch to about an inch, or any suitable thickness.

Similarly, upper portion 610 may have a length 620 that is similar or different than that of insertion portion 200. For example, length 600 may be from about one inch to about eight inches, from about two inches to about five inches, from about two and a half inches to about four inches, from about three to about three and a half inches, or any suitable length. The other dimensions of upper portion 610 may be of dimensions similar to those described with respect to insertion portion 200. Upper portion 610 may also have a connection element that facilitates or accomplishes connection between first portion 500 and second portion 510 of support 110.

Continuing with reference to FIG. 5A, an embodiment of second portion 510 is illustrated. Second portion 510 has height 630, width 640 and thickness 690, each of which may be any suitable magnitude. For example, height 630 may be from about one inch to about eight inches, from about two inches to about five inches, from about two and a half inches to about four inches, from about three to about three and a half inches, or any suitable height. For example, width 640 may be from about one half of one inch to about six inches, from about one inch to about three inches, from about one and a half inches and about two and a half inches, or any suitable width. For example, thickness 690 may be from about one eighth of an inch to about three inches, from about one quarter of an inch to about one and a half inches, from about a half an inch to about an inch, or any suitable thickness. In some embodiments thickness 690 and width 640 are greater than the corresponding dimensions of upper portion 610 of first portion 500 such that at least part of first portion 500 fits within second portion 510. Preferably, the dimensions are sufficiently greater such that the overall height of support 110 is adjustable by movement of second portion 510 along the y-axis over upper portion 610 of first portion 500 of support 110. In other embodiments, the dimensions of first portion 500 may be greater than those of second portion 510 such that at least a part of second portion 510 fits within first portion 500.

Second portion 510 also has first portion connector 700 and third portion connector 520. First portion connector 700 may be any suitable structure that facilitates connection between second portion 510 and first portion 500 of support 110. Preferably, first portion connector 700 interacts with an element on first portion 500 such that second portion 510 may be selectively moved relative to first portion 500. In some embodiments, first portion connector 700 is selectively engaged/disengaged with an element of first portion 500 by height adjustment button 540 (see FIG. 5B). In such embodiments, depressing height adjustment button 540 disengages first portion connector 700 and permits movement of second portion 510 relative to first portion 500 along the y-axis. Releasing height adjustment button 540 would then engage first portion connector 700 such that second portion 510 would be locked into place along the y-axis. In some embodiments, first portion connector 700 interacts with height adjuster 720 in third portion 560 (see FIG. 5B). In such an embodiment depressing height adjustment button 540 causes height adjuster 720 to interact with first portion connector 700 such that it disengages from the element in first portion 500, thereby permitting movement of second portion 510 along the y-axis relative to first portion 500.

Second portion 510 also has third portion connector 520. Third portion connector 520 may be any suitable structure that facilitates connection between second portion 510 and third portion 560. In the depicted embodiment, third portion connector is a cylindrical extension form second portion 510 that fits within orifice 680 (see FIG. 5B) of third portion 570. Third portion connector 520 and orifice 680 may have any suitable size and characteristics.

With reference now to FIGS. 5B and 5C, preferably, second portion connector 520 interacts with rotation adjuster 710 on third portion 560 such that third portion 560 may be selectively moved relative to second portion 510. In some embodiments, third portion connector 520 is selectively engaged/disengaged with rotation adjuster 710 by rotation adjustment button 550 (see FIG. 5B). In such embodiments, depressing rotation adjustment button 550 disengages third portion connector 520 from rotation adjuster 710 and permits movement of third portion 560 relative to second portion 510 along the w-axis. Releasing rotation adjustment button 550 would then engage second portion connector 520 from rotation adjuster 710 such that third portion 560 would be locked into place along the w-axis.

With reference again to FIGS. 5B and 5C, an embodiment of third portion 560 is illustrated. Third portion 560 has rotation adjustment button 550, height adjustment button 540, mandible arm receiver 530, main portion 570, orifice 680, rotation adjuster 710 and height adjuster 720. Although depicted as buttons, rotation adjustment button 550 and height adjustment button 540 may be any suitable structure that may be manipulated by a person. In addition, rotation adjustment button 550 and height adjustment button 540 may be placed on any suitable location on support 110 (even on each of the different portions described herein) or on other parts of the device. Preferably, rotation adjustment button 550 and height adjustment button 540 are positioned such that a person could place his/her hand on support 110 and interact with both.

Third portion 560 may have any suitable configuration and be any suitable shape. Thus, although in the illustrated embodiment third portion 560 is substantially circular, it may be any suitable shape. In preferred embodiments, third portion 560 rotates in a w-axis, such that mandible arm 120 moves in a w-axis. In some embodiments this movement aids positioning of mandible arm 120 with respect to a patient and, more specifically, the patient's jaw bone. Preferably, third portion 560 is configured such that it may be grasped and manipulated by a human hand. Thus, preferably a person could grasp third portion 560 such that the person could interact with rotation adjustment button 550 and height adjustment button 540 in a manner that would permit the person to adjust support 110, thereby adjusting/positioning mandible arm 120. By so doing, a person could then cause mandible arm 120 to contact a patient such that the patient may be placed and/or held in a desired position, for example the sniffing position.

Main portion 560 is depicted as circular, but it may be any suitable shape. Main portion 560 has height 650 and width 670, which may be equal or different and may have any suitable magnitude. For example, height 650 may be may be from one inch to about eight inches, from about two inches to about five inches, from about two and a half inches to about four inches, from about three to about three and a half inches about one half of one inch to about six inches, from about one inch to about three inches, from about one and a half inches and about two and a half inches, or any suitable height. For example, width 670 may be from one inch to about eight inches, from about two inches to about five inches, from about two and a half inches to about four inches, from about three to about three and a half inches about one half of one inch to about six inches, from about one inch to about three inches, from about one and a half inches and about two and a half inches, or any suitable length.

With reference again to FIGS. 5B and 5C, third portion 560 also has mandible arm receiver 530. Mandible arm receiver interacts with arm portion 340 of mandible arm 120 (see FIGS. 4A-4E). Mandible arm receiver 530 may have any suitable length. For example, mandible arm receiver 530 may be from about one eighth of an inch to about three inches, from about one quarter of an inch to about one and a half inches, from about a half an inch to about an inch, or any suitable thickness. Mandible arm receiver 530 may also have any suitable configuration and/or shape. Thus, although in the depicted embodiment mandible arm receiver 530 may be substantially cylindrical, it may be any suitable structure. In the depicted embodiment distal end 360 (see FIG. 4A) is inserted into mandible arm receiver 530 and mandible arm receiver 530 holds mandible arm 120 in place via its connection with arm portion 340. Arm portion 340 may be removably, adjustably or fixedly attached to mandible arm receiver 530 and arm portion 340 may be integral with mandible arm receiver 530. Mandible arm receiver 530 may also have a release button 370. Release button 370 directly or indirectly interacts with arm portion 340 to permit insertion and/or removal of arm portion 340 into and/or from mandible arm receiver 530. Release button 370 may also permit adjustment of the extent of insertion of arm portion 340 into mandible arm receiver 530, such that the distance between mandible arm 120 and third portion 560 may be increased or decreased. Such movement would also permit adjustment of mandible gap 150 (see FIG. 1). Release button 370 may be any suitable structure, including a button, latch, switch or dial. Release button 370 may also be placed on any suitable location on the device.

In some embodiments arm portion 340 has flat portion 350 that interacts with a surface within mandible arm receiver 530. In some embodiments, this interaction prevents one from inserting the right mandible arm 120 into the left support 110, and vice-versa.

With reference now to FIG. 5C, in certain embodiments, mandible arm 120 may be connected to third portion 560 in a manner that permits movement of mandible arm 120 relative to support 110. For example, mandible arm 120 may be movable in one or more axes, including the x, y and z axes relative to support 110. In such embodiments the movement of mandible arm 120 may facilitate placing and/or maintaining a patient in a desired position, including the sniffing position.

In addition to the various devices described herein, the present invention also includes methods. Generally, the methods of the present invention relate to placing and/or maintaining a patient in a desired position. In some embodiments, this is a position that facilitates regular or semi-regular breathing by a patient that is under sedation or general anesthesia. For example, the desired position may be the sniffing position. The methods may include the use of various equipment, such as an $O_2$ or face mask with associated tubing in order to provide mask ventilation, various other breathing apparatuses, including tubes at least partially inserted into the patient. Various embodiments of the methods include the use of the devices described herein. For example, a patient may be placed in a desired position, and then a device of the present invention may be adjusted to maintain the patient in a desired position. In other embodiments, a device of the present invention may be used to place the patient in a desired position. In further embodiments, a device of the present invention may be used to place and maintain a patient in a desired position. In some embodiments, the methods provide a quick and easy method of positioning a patient with a single interaction with a device. In some embodiments, the methods permit one to position the patient in a single movement or in a single contact with a device of the present invention.

Figure 6:
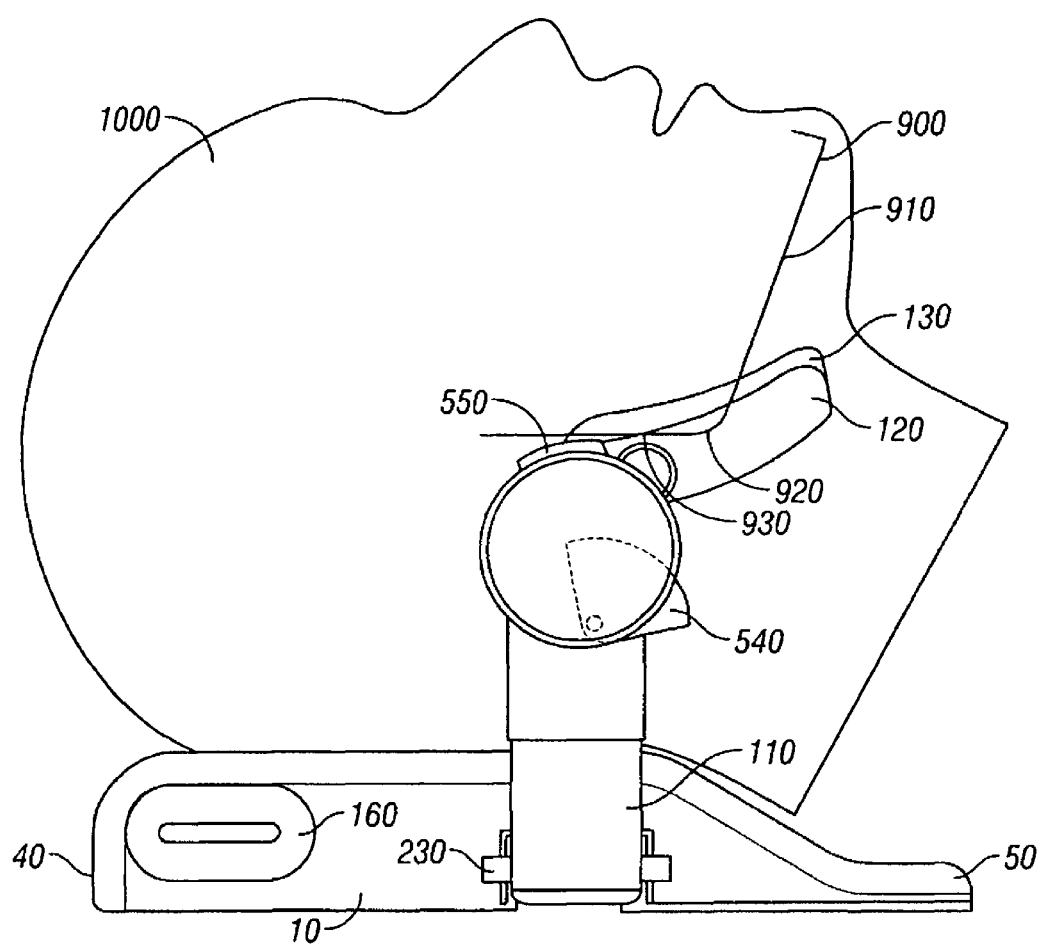
FIG. 6 is a schematic diagram providing a side view of an embodiment of a device of the present invention.

By way of example, and with reference to FIG. 6, a device according to the present invention may be appropriately positioned using, or not using, gripping element 160 to manipulate and position base 10 on a gurney, operating table, dentists' chair or any other suitable place. A patient 1000 could be placed on a device of the present invention having base 10 such that the top of the patient's head is oriented with upper side 40 of base 10 and the patient's neck would be oriented with lower side 50 of base 10. Such placement could be done before or after positioning of base 10. The patient could be appropriately placed on base 10 with or without reference to an alignment guide 155 (see FIG. 1). For example, a patient 1000 may be positioned such that the patient's mouth is approximately in line with supports 110 (and/or alignment guide 155). Once positioned (or in some embodiments, as the patient 1000 is positioned), mandible gap 150 (see FIG. 1) may be adjusted by moving support 110 along the x-axis, thereby increasing support width 140. In some embodiments, this may be done by pressing button 230 on support 110 and moving support toward or away from base 10 until support 110 is in a desired position and then releasing button 230 to lock support 110 in place. In addition, support 110 may also be adjusted in the y-axis. In some embodiments, this may be done by depressing height adjustment button 540 and moving support 110 in the y-axis until support 110 is in a desired position and then releasing height adjustment button 540. Moreover and as necessary, support 110 may also be adjusted in the w-axis or the z-axis. In some embodiments, this may be done by depressing rotation adjustment button 550 and moving support 110 in the w-axis until support 110 is in a desired position and then releasing rotation adjustment button 550. Such procedure may be repeated for the support 110 on the other side of base 10. In some embodiments support 110 is positioned relative to patient 1000 such that rotational movement of support 110 (and mandible arm 120) in the w-axis may tilt the patient's head back such that the patient's airway is opened.

The various adjustments (done only as necessary) may be done until mandible arm 120 contacts the patient in such a way that the patient is placed and/or maintained in a desired position. For example, adjustment(s) may be made until mandible pad 130 contacts one or more points of the patient's jaw. In some embodiments, the adjustment(s) will be made until the mandible pad 130 contacts the ramus 930 of a patient's jaw, the body 910 of the patient's jaw and the angle 920 of a patient's jaw.

Thus, it is seen that devices and methods are provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

While various embodiments of the present invention have been described above, it should be understood that they have been presented by way of example only, and not of limitation. Likewise, the various figures may depict an example configuration for the invention, which is done to aid in understanding the features and functionality that may be included in the invention. The invention is not restricted to the illustrated example configurations, but the desired features may be implemented using a variety of alternative configurations. Indeed, it will be apparent to one of skill in the art how alternative functional, logical or physical configurations may be implemented to implement the desired features of the present invention. Also, a multitude of different constituent part names other than those depicted herein may be applied to the various parts or elements. Additionally, with regard to method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary block diagrams and other illustrations. As will become apparent to one of ordinary skill in the art after reading this document, the illustrated embodiments and their various alternatives may be implemented without confinement to the illustrated examples. For example, the figures and their accompanying description should not be construed as mandating a particular configuration, including a particular geometry of the various parts and elements.

What is claimed is:

1. A device comprising:
    a base comprising a first surface, a second surface, and a third surface wherein the base is configured to substantially accommodate a patient's head disposed on the third surface;
    a first support positioned on the first surface of the base and lockably adjustable with respect to the first surface of the base in an x axis and lockably adjustable with respect to the third surface in a y axis;
    a second support positioned on the second surface of the base and lockably adjustable with respect to the second surface of the base in the x axis and lockably adjustable with respect to the third surface in the y axis;
    a first mandible arm extending from a first rotatable portion of the first support, wherein the first rotatable portion is lockably rotatable in a w axis to lockably adjust the first mandible arm with respect to the w axis, and wherein the first mandible arm is positionable to be in contact with the patient's jaw; and
    a second mandible arm extending from a second rotatable portion of the second support, wherein the second rotatable portion is lockably rotatable in the w axis to lockably adjust the second mandible arm with respect to the w axis, and wherein the second mandible arm is positionable to be in contact with the patient's jaw;
    wherein the first mandible arm and the second mandible arm are movable such that each is positionable to be in contact with the patient's jaw and to maintain the patient in a desired position.

2. The device of claim 1, wherein the mandible arm is positionable to be in contact with the patient's jaw at a ramus, a body, or an angle of the patient's jaw.

3. The device of claim 2, wherein each of the first mandible arm and the second mandible arm is positionable such that the mandible pad is in contact with the patient's jaw at two or more of a ramus, a body, or an angle of the patient's jaw.

4. The device of claim 3, wherein each of the first mandible arm and the second mandible arm is positionable such that the mandible pad is in contact with a patient's jaw at a ramus, a body, and an angle of the patient's jaw.

5. The device of claim 2, wherein the mandible pad comprises foam.

6. The device of claim 1, wherein the first support is movable relative to the base and the second support is movable relative to the base.

7. The device of claim 6, wherein the first support is movable relative to the base in two axes and the second support is movable relative to the base in two axes.

8. The device of claim 6, wherein the first support is movable relative to the base in three axes and the second support is movable relative to the base in three axes.

9. The device of claim 1, wherein the base is rectangular.

10. The device of claim 1, wherein the first mandible arm and the second mandible arm each comprise a mandible pad.

11. The device of claim 1, wherein the first mandible arm and the second mandible arm are removably connected to the first support and the second support, respectively.

12. The device of claim 1, wherein the first mandible arm is movable relative to the first support and the second mandible arm is movable relative to the second support.

13. The device of claim 1, wherein the desired position is the sniffing position.

14. The device of claim 1, wherein the first support is movable relative to the first mandible arm and the second support is movable relative to the second mandible arm.

15. A method for positioning a patient comprising the steps of:
    providing the device of claim 1;
    placing the patient's head substantially on the base; placing the patient's head in a desired position; moving the first mandible arm to contact the patient's jaw; moving the second mandible arm to contact the patient's jaw; wherein the contact of the first mandible arm and the second mandible arm provides sufficient force to substantially maintain the patient's head and/or jaw in a desired position.

16. The device of claim 1, wherein the first mandible arm extends from a circumference of the first rotatable portion, and wherein the second mandible arm extends from a circumference of the second rotatable portion.

17. The device of claim 1, wherein the base further comprises a head rest disposed on the third surface configured to provide flexion of the patient's neck by elevation of the patient's head.

18. The device of claim 1, wherein the first and second mandible arms are configured to extend the patient's head when rotated in the w-axis.

19. The device of claim 1, wherein the plurality of mandible arms are configured to extend the patient's head when rotated in the w-axis.

20. The device of claim 1, wherein the first and second supports and first and second rotatable portions are adjustable while the patient is in contact with the first and second mandible arms.

21. A mandible arm comprising:
a curved portion, wherein the curved portion is substantially rigid;
a mandible pad, wherein the mandible pad is flexible, and wherein the mandible pad has a distal side configured to attach to the curved portion and a proximal side configured to contact a patient's jaw at a at least two of a ramus, a body, and an angle of the patient's jaw; and
a connector portion, wherein the connector portion is configured to extend from and attach to a rotatable portion of a support, and wherein the connector portion is further configured to attach to a support that is attached to a base comprising a left side and a right side, wherein the base is configured to substantially accommodate a patient's head, and wherein the support is movable in three axes such that the mandible pad is positionable to be in contact with a patient's jaw at one or more points and to maintain a patient in a desired position.

* * * * *